United States Patent [19]

Barber

[11] Patent Number: 4,612,922
[45] Date of Patent: * Sep. 23, 1986

[54] DRILLING APPARATUS AND METHOD

[76] Inventor: Forest C. Barber, 2925 Race St., Fort Worth, Tex. 76111

[ * ] Notice: The portion of the term of this patent subsequent to Aug. 23, 2000 has been disclaimed.

[21] Appl. No.: 525,486

[22] Filed: Aug. 22, 1983

Related U.S. Application Data

[62] Division of Ser. No. 227,389, Jan. 22, 1981, Pat. No. 4,399,813.

[51] Int. Cl.[4] .................................................. A61F 5/04
[52] U.S. Cl. .............................. 128/92 EB; 128/92 R
[58] Field of Search ............ 128/92 R, 92 EB, 92 EC

[56] References Cited

U.S. PATENT DOCUMENTS

| | | | |
|---|---|---|---|
| 2,638,092 | 5/1953 | Dorr | 128/92 R |
| 4,237,875 | 12/1980 | Termanini | 128/92 BA |
| 4,399,813 | 8/1983 | Barber | 128/92 EB |

FOREIGN PATENT DOCUMENTS

| | | | |
|---|---|---|---|
| 735333 | 5/1943 | Fed. Rep. of Germany | 128/92 EC |
| 197710 | 10/1977 | U.S.S.R. | 128/92 EC |

OTHER PUBLICATIONS

Rockwell International, 400 N. Lexington Ave., Pittsburgh, PA 15208, 1982 Industrial Machinery Catalog, pp. A1-A8.

*Primary Examiner*—Gene Mancene
*Assistant Examiner*—C. W. Shedd
*Attorney, Agent, or Firm*—Peter J. Murphy

[57] ABSTRACT

A drill assembly includes a handle carrying a mount for a pneumatic drill motor, and an elongated tubular support enclosing an extended motor shaft which carries a drill bit chuck projecting from the end of that support. The drill assembly coacts with a drill guide assembly including an elongated tubular guide for receiving the tubular support in sliding relation, and having a rotary bearing at its lower end for rotationally supporting the drill bit. The lower end face is concave to enable seating on the prosthesis tip to be drilled. The drill guide assembly includes an offset handle and a stop clamp and depth gauge for coaction with the drill assembly handle to control the depth of drilling.

14 Claims, 10 Drawing Figures

DRILLING APPARATUS AND METHOD

This application is a division of application Ser. No. 227,389, filed Jan. 22, 1981, now U.S. Pat. No. 4,399,813.

BACKGROUND OF THE INVENTION

This invention relates to manual drilling apparatus, and more particularly to apparatus for drilling into the end of a metallic prosthesis fragment which remains securely embedded in skeletal bone after fracture of the prosthesis and removal of the relatively free portion of the fractured prosthesis.

Possibly as the result of an accident or a war injury, or the crippling effects of bone disease, it is sometimes desirable to replace a joint of the human body with an artificial joint. The total replacement of joints, and the consequent possibility of a future revision of a surgically implanted joint, is a relatively new field of surgery. Its development is being enhanced by the discovery, and application in the surgery field, of newer and stronger metals and of new plastics and similar materials. For example, a total hip replacement consists of replacing the existing acetabular cup with a polymer polyethylene plastic cup, and replacing the rounded head of the femur with a metal prosthesis including a ball which coacts with the plastic cup and an elongated stem which is extended into and embedded in the intramedullary canal of the femoral shaft. Even though this metal femoral component of the prosthesis is constructed of extremely hard metal, because of all of the stress and strain that is placed upon it by the action of the human body in the performance of its daily routine, it sometimes happens that the shaft of the prosthesis will fracture; and replacement of the entire femoral component will then be necessary in order to allow the wearer to remain ambulatory without experiencing considerable pain. The difficulty of extracting the tip portion of a fractured prosthesis stem is readily apparent when one considers that this tip portion is implanted possibly deep within the intramedullary canal of the bone and possibly embedded within surgical cement, and that the surgical area is confined considering the narrow size of the bone shaft.

This invention is particularly concerned with the aspect of revision surgery which involves the removal of an earlier implanted prosthesis which has fractured, in order to enable implantation of a replacement prosthesis. While the invention is concerned broadly with drilling apparatus, the invention will be described with particular reference to hip revision surgery.

One approach which has been used in the past to remove the embedded tip of the femoral stem of a hip joint prosthesis involves the removal of the surgical cement from the annular space between the stem and the femoral cortex. Tools for this procedure may include osteotomes or power instruments. Because this annular space is usually very narrow, it may be difficult to remove the cement around the broken stem for a distance sufficient to allow it to be dislodged. Moreover, because of this confined space, a frequent complication of this procedure is the perforation of the cortex. This complication may require bone grafting and the use of a long-stem femoral component for the revision implant. The use of such long stem femoral component further compounds the complication, since the achieving of excellent cement distribution and pressurization is much more difficult with the use of such long-stem component, especially if there is a hole in the femur. In addition, the future surgical revision of the long-stem femoral component, should it fail, increases the technical difficulties.

Another known approach for the removal of the embedded tip of a prosthesis stem involves creating a window in the cortex of the femur to enable the driving of the stem toward the cut surface of the femoral neck through the use of a driving tool such as a carbide chisel. One complication of this procedure is that the creating of the window in the femur produces a stress riser which weakens the femur and predisposes this area to fracture. To overcome the resulting femoral weakness, it is necessary to use a long-stem component for the replacement prosthesis, in order to bypass the stress riser. Complications accompanying the long-stem component have been discussed above. Accessory fixation and/or bone grafting may also be required. With this approach, a possible mechanical problem may result from the use of extremely hard so-called space-age metals in the fabrication of the original prosthesis. With such metals it is sometimes difficult, even with a carbide tip chisel, for example, to penetrate the surface of the prosthesis sufficiently to enable it to be driven by the chisel.

The concept of drilling into the fractured proximal end of the embedded prosthesis tip and locking into that drilled hole with some form of extractor device to enable withdrawing of the prosthesis tip, without resorting to either of the above described techniques or approaches, is attractive. One known technique, embodying this concept, involves drilling into the distal end of the stem and utilizing a screw threadedly engaged within the drilled hole as an extractor. While this technique may be useful where the prosthesis has been fabricated from stainless steel or other material having the equivalent or lesser hardness, this technique is not suited for use with prostheses constructed of the harder spage-age metals and alloys.

SUMMARY OF THE INVENTION

A principal object of this invention is to provide novel drilling apparatus for manual drilling operations.

Another object of this invention is to provide manual drilling apparatus including novel means for manually supporting and guiding that apparatus.

A further object of this invention is to provide manual drilling apparatus including novel means for controlling the depth of drilling.

Still another object of this invention is to provide novel drilling apparatus for drilling into the end of an elongated narrow object.

A still further object of this invention is to provide a novel apparatus for drilling into a prosthesis embedded in a bone shaft, without the necessity or possibility of perforating the bone cortex.

These objects are accomplished in apparatus which includes the following. A drill assembly includes an elongated tubular support, a drill motor mounted at one end of that tubular support and having a drive shaft extending through that support, and a drill chuck mounted at the end of the drive shaft which projects from the support. A drill guide assembly includes an elongated tubular drill guide which is dimensioned to receive and guide the tubular support for relative axial and rotational movement. One end of the drill guide has means for locating that end relative to an object to be drilled. The drill guide assembly further includes means for limiting axial movement of the drill assembly relative to the drill guide assembly.

More particularly the drill assembly includes a support handle extending laterally from its elongated drill support, and the drill guide assembly includes a support handle extending laterally from its support shaft. These support handles enable independent manual support of the drill assembly and the drill guide assembly.

The novel features and the advantages of the invention, as well as additional objects thereof, will be understood more fully from the following description when read in connection with the accompanying drawings.

DRAWINGS

FIG. 3 is a fragmentary view, partially in section, showing details of the drill assembly;

FIG. 3A is a fragmentary, sectional, detailed view of the rotary bearing of the drill assembly;

DESCRIPTION OF THE PREFERRED EMBODIMENT

This invention has particular application to the drilling into the end of a fragment of an elongated prosthesis, which remains embedded in skeletal bone after fracture of the prosthesis.

Figure 1:
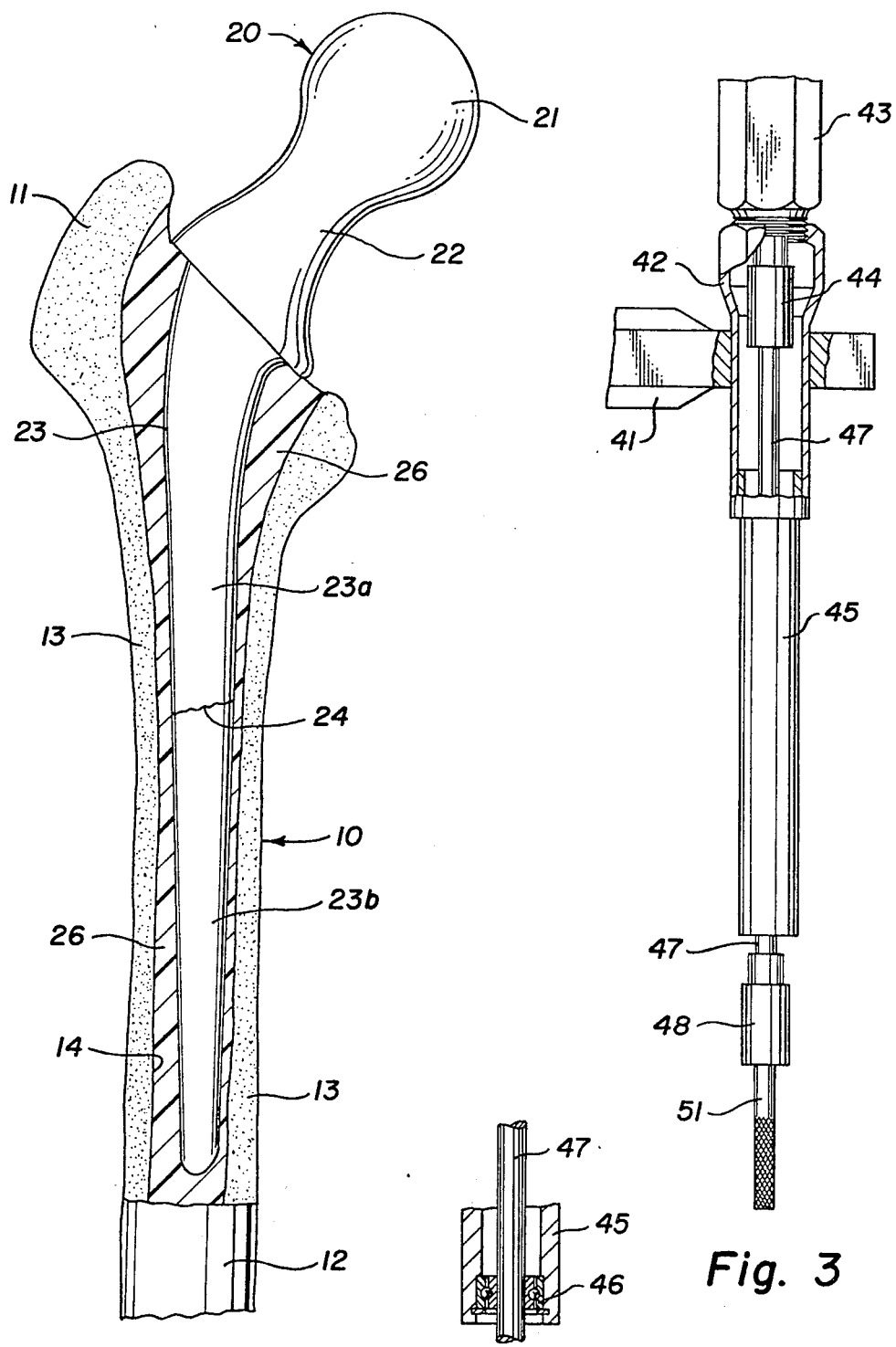
FIG. 1 is a sectional view of the upper end of a femur with the fractured femoral component of a total hip replacement in place.

As background for the following description of the apparatus of the invention, FIG. 1 illustrates the upper portion of a human femur along with the femoral component of a total hip replacement. The illustrated femur may be the femur of the right leg as viewed from the front. Referring to FIG. 1, the illustrated position of a femur 10 includes a portion of the upper enlarged head 11 and a portion of the stem 12. The portion of the head 11 which forms the ball portion of the hip joint has been removed and is replaced by a portion of the implanted prosthesis which is the femoral component 20. This femoral component is formed from a suitable metal, and includes an enlarged spherical ball portion 21 which forms the ball portion of the hip replacement joint, a neck portion 22 which spaces the ball from the head 11 of the femur, and an elongated stem 23 extending from the neck to be embedded within the femur stem. The prosthesis stem 23 has been implanted within the intramedullary canal 14 of the femur, and the annular space between the prosthesis stem and the cortex 13 of the femur has been filled with surgical cement 26 to provide for secure embeddment of the prosthesis within the bone.

To illustrate the problem to which the present invention is directed, FIG. 1 illustrates a fracture 24 of the prosthesis stem 23 within the femur, and without fracture of the femur itself; with a proximal portion of the prosthesis stem 23a remaining integral with the neck and head, and with the distal portion 23b of the prosthesis stem being embedded deep within the intramedullary canal. While a fracture of the prosthesis stem may occur at any point from a point near the neck portion 22 to a point very close to the proximal end, this separated proximal portion 23b will be referred to as the "tip" of the prosthesis or of the femoral component even though this tip may have substanial length.

For revision surgery following a fracture of the type illustrated in FIG. 1, the femur is preferably displaced from the hip bone sufficiently to allow generally axial access to the intramedullary canal. The proximal portion of the femoral component 20, including the stem portion 23a, has probably become sufficiently loosened from the embedding surgical cement, as a result of the fracture, to allow ready removal from the femur. As further background for the detailed description of the apparatus of the invention which follows, the surgical procedure includes, very broadly, the following steps: (1) removal of the surgical cement which had surrounded the removed prosthesis stem 23a to provide an enlarged access canal to the embedded tip 23b; (2) forming a hole in the exposed end of the embedded tip 23b which is generally aligned with the access canal and the longitudinal axis of the prosthesis tip, and forming a lateral undercut within that hole; (3) engaging the prosthesis tip with an extractor tool having an axial shaft to enter the hole and having a laterally projecting toe to be received in the undercut of that hole, and locking the toe of the extractor tool within the undercut; and (4) exerting a suitable axial force on the extractor tool to dislodge the prosthesis tip from the hold of the femur shaft and/or the surgical cement.

The apparatus of the invention is conveniently described as consisting of two separate assemblies, namely: (1) a drill guide assembly; and (2) a drill assembly. The drill guide assembly and the drill assembly are shown in coacting relation in FIG. 2. The drill assembly is shown in additional detail in FIGS. 3 and 8.

Figure 5:
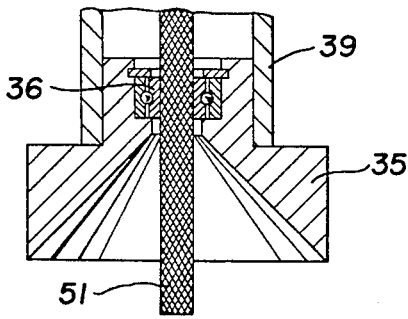
FIG. 5 is a fragmentary, sectional, detailed view of the rotary bearing of the drill guide assembly.

For convenience of description, reference will be made to the upper and lower ends of various components of the drill guide assembly and drill assembly, having reference to the orientation of FIG. 2. The drill guide assembly 30 includes a base shaft 31 having an offset handle 32 fixed to the upper end of the shaft to be grasped by the operator, and having an offset bracket 33 fixed to the lower end of the shaft and extending in the opposite direction. The offset bracket 33 is provided with an internally threaded hole at its end opposite from the shaft 31; and a guide sleeve 34 having an upper threaded end is threaded into the guide bracket hole and extends parallel to the shaft 31. A head 35 is mounted at the lower end of the guide sleeve; and this head is provided with a frusto-conical end face for centering the drill guide assembly on the prosthesis tip as will be described. As best seen in FIG. 5, the head 35 carries an anti-friction bearing 36 for centering the drill bit. A depth stop 37 in the form of a C-clamp is mounted on the shaft 31 and includes a clamping screw 38 for securing the depth stop at the desired elevation relative to the guide sleeve head 35. A depth gauge 39 consists of a rectangular block having a hole at one end by means of which it is slidably and rotatably mounted on the shaft 31 above the depth stop. The depth gauge has a selected thickness, ¼ inch for example, to control the depth of drilling as will be described.

The drill assembly 40 includes an elongated handle 41 to be gripped by the operator, the handle carrying a motor mount 42 adjacent to one end, the motor mount consisting of a tubular shank having a threaded box at its upper end, the axis of this motor mount being perpendicular to the length of the handle. A high speed pneumatic drill motor 43 includes a threaded pin at the lower end of the housing for engagement with the motor mount 42 and a drive shaft and associated drill bit chuck 44 extend from this end of the motor housing. A suitable drill motor is the Midas Rex Whirlwind Drill Motor, manufactured by Midas Rex Pneumatic Tool Company of Fort Worth, Tex., which drill motor has an output shaft capability of 73,000 rpm. A guide sleeve 45 is mounted concentrically with the motor mount 42 and extends downwardly from the handle 41. As best seen in FIGS. 3 and 3A, the lower end of the guide sleeve carries an anti-friction bearing 46 for rotationally guiding the lower end of a motor extension shaft 37 which carries a drill chuck 38 at its lower end. The extension shaft is inserted through the bearing at the lower end of the guide sleeve, and its upper end is secured in the motor chuck 44.

Figure 2:
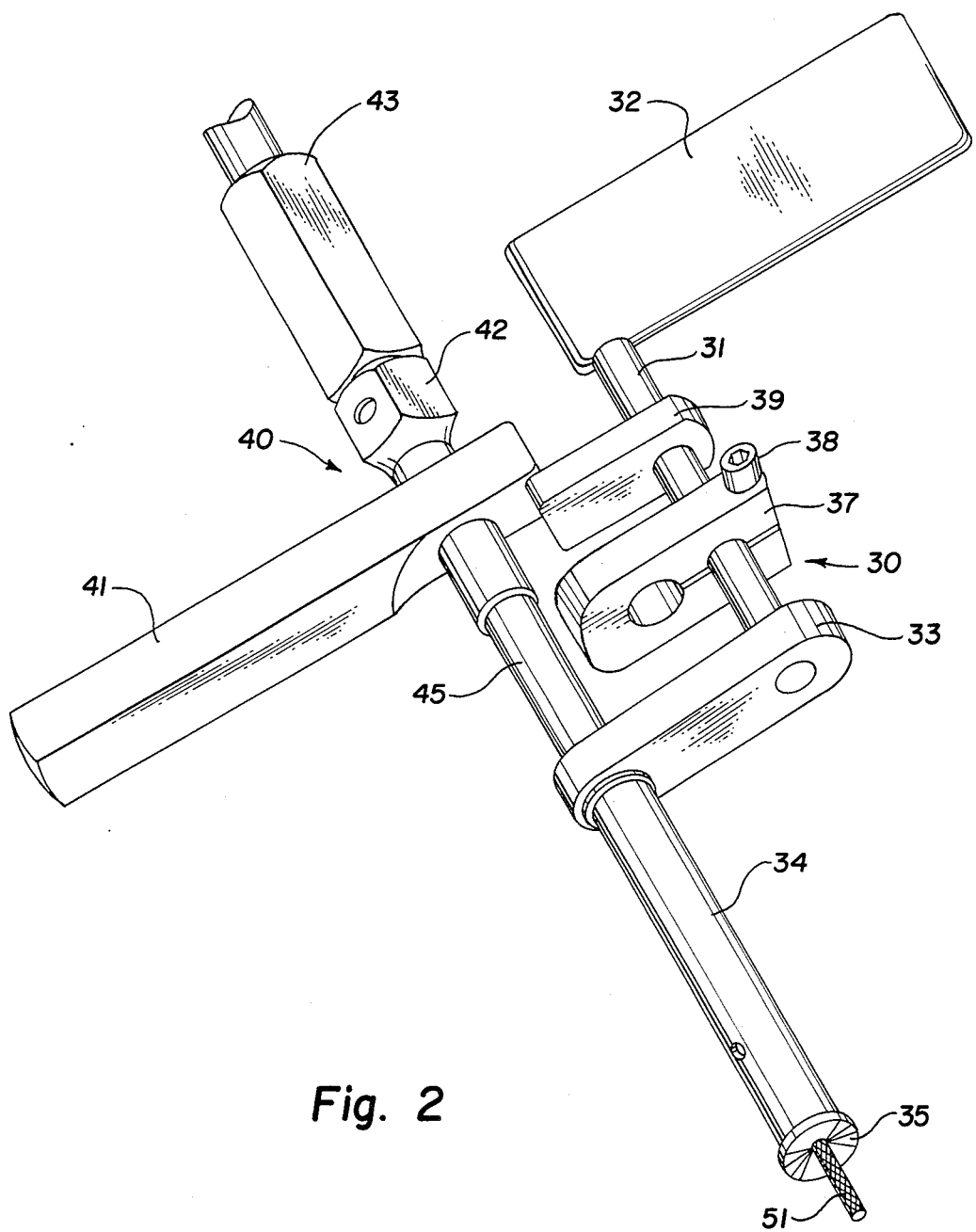
FIG. 2 is a perspective view showing the drill guide assembly and drill assembly in coacting relation.

FIGS. 2 and 3 illustrate a straight end cutting drill bit 51 used for the initial cutting to be described. The internal diameter of the guide sleeve 34 and the external diameter of the guide sleeve 45 are dimensioned that the latter sleeve will fit within the former with a relatively close sliding fit; and the guide sleeve bearing 36 is dimensioned to receive in close fitting relation the shank of the end cutting bit 51 which extends through this bearing and projects from the lower end of the guide sleeve 34.

Figure 4:
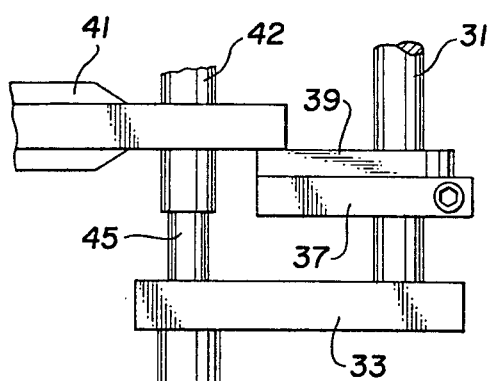
FIGS. 4 and 6 are fragmentary side views showing operational relationships of the drill guide assembly, drill assembly, and embedded prosthesis tip.
Figure 6:
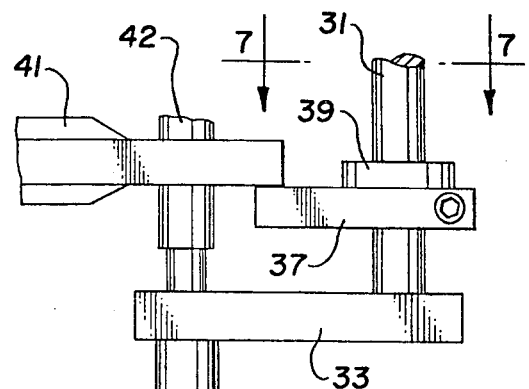

FIGS. 4 through 7 particularly illustrate the relationships of the drill guide assembly 30 and drill assembly 40 to each other, and also to the fractured prosthesis tip 23b embedded within the femur 10 for the drilling of a generally axial hole into the exposed end of the tip. As seen in FIGS. 4 and 6, the surgical cement 26 has been removed from the intramedullary canal 14 to a depth somewhat below the fractured end face of the tip. This removal of the surgical cement might well be accomplished with the use of a suitable long, narrow cutting bit mounted directly in the motor chuck 44 of the above mentioned drill motor 43. The cement must be completely removed from around the upper end of the tip 23b so that the concave, frusto-conical end face of the drill guide head will fit over the tip end and seat firmly over the segment to prevent the drill guide and drill bit from wandering laterally once drilling begins. Ideally, the drill guide could be centered relative to the tip 23b so that the walls surrounding the drill hole will be sufficiently thick.

Figure 7:
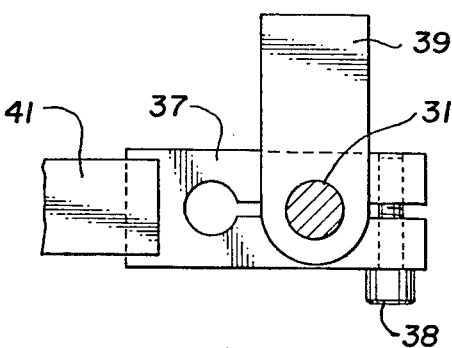
FIG. 7 is a fragmentary detailed view taken along the line 7—7 of FIG. 6.

FIG. 4 illustrates the setting up of the assemblies to begin drilling. The drill guide head 35 is located firmly relative to the prosthesis tip 23b, the depth stop 37 is released from clamping engagement with the shaft 31 to enable the drill assembly 40 to be moved downward to the point where the cutting end of the bit 51 just engages the fractured surface of the tip 23b. In this condition, the depth gauge 39 is placed in overlying relation to the depth stop 37, as seen in FIG. 4, and these two members are moved upwardly on the shaft 31, in interference relation with the handle 41 to the point where the upper face of the gauge 39 engages the lower face of the handle 41. The depth stop 37 is then clamped in this position on the shaft by means of the clamping screw 38. For the drilling operation the depth gauge 39 is moved out of interference position, as seen in FIGS. 6 and 7; and this allows the drilling of a hole to a depth determined by the interference engagement of the handle 41 with the stop 37. That completes the drilling of a generally axially aligned hole 27 of desired diameter and depth; and the drill guide assembly 30 is no longer needed.

Figure 8:
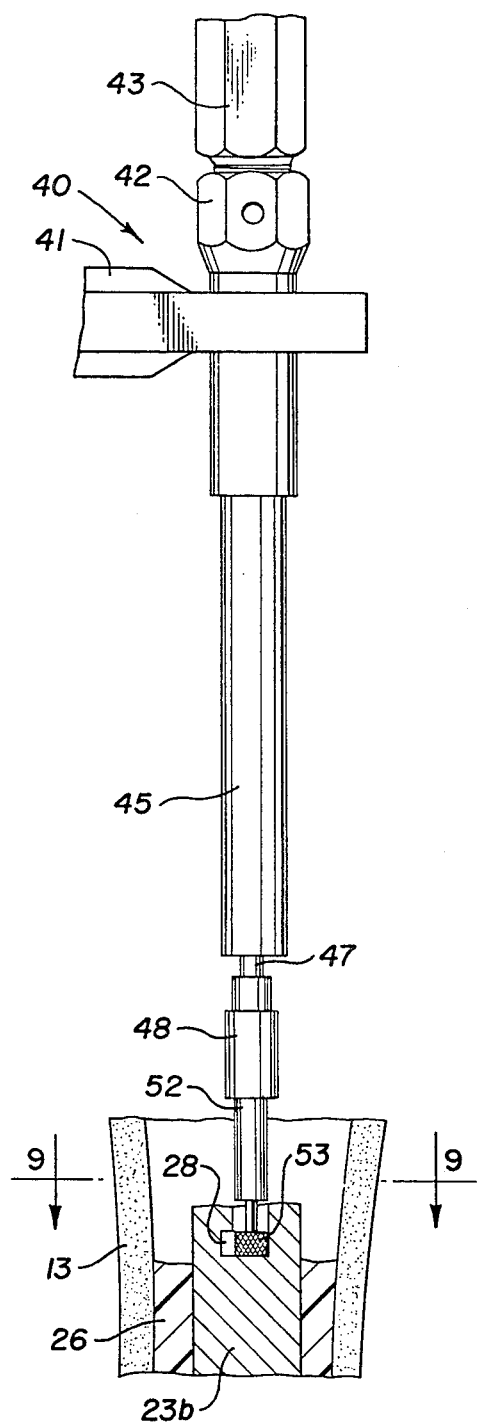
FIG. 8 is a side view of the drill assembly showing the undercutting drilling operation.
Figure 9:
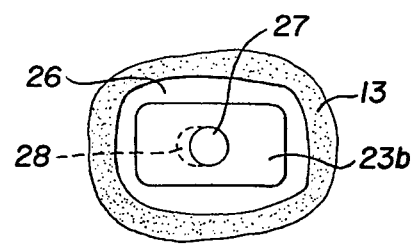
FIG. 9 is a detail view taken along the line 9—9 of FIG. 8.

The second drilling operation involves the cutting of an undercut recess 28 in the side wall of the hole 27 to provide a downward facing ledge. This operation is best illustrated in FIGS. 8 and 9; and for this operation an undercut drill bit 52 is mounted in the extension shaft chuck 48 of the drill assembly. The bit 52 has the same overall diameter as the straight bit 51; and is provided with a side cutting head 53 at its distal end joined to the remainder of the bit shank by a reduced diameter neck 54. This bit is inserted into the hole 27 and, with moderate side pressure on the drill assembly, the undercut recess 28 formed at only one side of the hole as seen in the drawing.

The extractor apparatus for coacting with the drilled hole and undercut 27, 28, is described in the parent application Ser. No. 227,389, now U.S. Pat. No. 4,399,813.

What has been described are a unique apparatus and method which are particularly adapted for the controlled drilling into the end of an elongated member.

An advantage of the invention is that it enables the controlled drilling into an object of difficult access, such as a fragment of a fractured prosthesis, and provides means for the orientation and aligning of the drill by two persons.

The use of this drilling apparatus and method enables a technique for withdrawing the prosthesis fragment, which technique eliminates the need for deliberately providing an aperture or window in the cortex of the femur. An additional advantage of the technique is that it minimizes the possibility of an inadvertent penetration of the cortex.

While preferred embodiments of the invention have been illustrated and described, it will be understood by those skilled in the art that changes and modifications may be resorted to without departing from the spirit and the scope of the invention.

What is claimed is:
1. Apparatus for manual drilling comprising
a drill assembly including an elongated tubular support, handle means mounted on said tubular support to enable manual support and guiding of said drill assembly, a drill motor mounted at one end of said tubular support having a drive shaft extending therethrough, and drill chuck means mounted at the end of said shaft projecting from said support;
a drill guide dimensioned to receive and guide said tubular support for relative axial and rotational movement, handle means mounted on said drill guide to enable manual support and guiding thereof;
said drill guide and said drill assembly having coacting means for limiting axial movement of said drill assembly relative to said drill guide.
2. Apparatus as set forth in claim 1
said drill including bearing means disposed within the lower end of said tubular support for rotationally supporting the lower end of said drive shaft; said drill guide assembly including bearing means disposed in the lower end thereof for rotationally supporting a drill bit mounted in said drill chuck means.

3. Apparatus as set forth in claim 1
said drill guide including a support shaft mounted in parallel offset relation therewith; a stop member mounted in sliding relation on said support shaft and disposed for interfering relation with said drill assembly, said stop member having clamp means for securing said member in selected position on said shaft;
a depth gauge rotatably mounted on said shaft and disposed for overlying relation with said stop member and interfering relation with said drill assembly.

4. Apparatus as set forth in claim 3
said drill assembly handle means including a support handle extending laterally from said elongated drill support;
said drill guide including a support handle extending laterally from said support shaft;
said support handles enabling independent manual support and guiding of said drill assembly and said drill guide.

5. Apparatus as set forth in claim 1
said drill guide including an adjustable stop member mounted for movement parallel to the longitudinal axis of said drill guide and disposed for interfering relation with said drill assembly, said stop member having means for securing said member in a selected position;
a depth gauge mounted in overlying relation with said stop member, being movable relative to said stop member for selective interfering and noninterfering relation with said drill assembly.

6. Apparatus as set forth in claim 1
one end of said drill guide, associated with the drill chuck end of said tubular support, having means for locating said one drill guide end relative to an object to be drilled.

7. A manual drilling method comprising the steps
fabricating a drill assembly to include an elongated tubular support, a rotary drill motor mounted at one end of said support, an elongated drive shaft coupled at one end to said motor and rotatably supported in said tubular support, and a drill chuck nonrotatably mounted at the other end of said drive shaft;
supporting said drill assembly in a drill guide dimensioned to receive and guide said tubular support for relative rotational and axial movement;
providing fixed handle means on each of said drill guide and said drill assembly to enable the manual guiding of each assembly;
and providing coacting interference members on said drill guide and said drill assembly for limiting axial movement of said drill assembly toward said one end of said drill guide.

8. A drilling method as set forth in claim 7 including the step
providing said coacting interference members with adjustment means for selecting the limit of movement of said drill assembly toward said one end of said drill guide assembly.

9. A drilling method as set forth in claim 7 including the steps
forming said handle means on said drill assembly as an elongated handle extending laterally from said tubular support;
and forming said handle means on said drill guide as an elongated handle extending laterally therefrom.

10. A method as set forth in claim 7 including the step
providing a locating means at one end of said drill guide for locating said one end thereof relative to an object to be drilled.

11. A method for drilling a hole manually comprising the steps
drilling a hole with a drill assembly which includes an elongated tubular support, a rotary drill motor mounted at one end of said support, an elongated drive shaft coupled at one end to said motor and rotatably supported in said tubular support, and a drill chuck nonrotatably mounted at the other end of said drive shaft;
supporting said drill assembly in a drill guide which is dimensioned to receive said drill assembly from one end and to guide said tubular support for relative rotational and axial movement;
guiding and controlling both said drill guide and said drill assembly by means of respective handle means fixed thereto;
and limiting axial movement of said drill assembly toward said other end of said drill guide by means of coacting interference members mounted thereon.

12. A method as set forth in claim 11 including the step
adjusting at least one of said coacting interference members relative to its respective assembly, for selecting the limit of movement of said drill assembly toward said other end of said drill guide.

13. A drilling method as set forth in claim 11 including the steps
guiding and controlling said drill assembly by means of an elongated handle extending laterally from said tubular support;
and guiding and controlling said drill guide by means of an elongated handle extending laterally therefrom.

14. A method as set forth in claim 11 including the steps
forming locating means at the other end of said drill guide for locating said other end relative to an object to be drilled;
locating said drill guide relative to said object to be drilled by means of said locating means.

* * * * *